United States Patent [19]

Spector

[11] Patent Number: 4,695,434
[45] Date of Patent: * Sep. 22, 1987

[54] AROMA-GENERATING UNIT

[76] Inventor: Donald Spector, 380 Mountain Rd., Union City, N.J. 07087

[*] Notice: The portion of the term of this patent subsequent to Aug. 24, 1999 has been disclaimed.

[21] Appl. No.: 412,080

[22] Filed: Aug. 27, 1982

[51] Int. Cl.$^4$ .............................................. A61L 9/04
[52] U.S. Cl. .................... 422/116; 239/56; 239/57; 422/4; 422/124; 422/125
[58] Field of Search ................ 422/4, 116, 124, 125, 422/305, 306; 239/56, 57

[56] References Cited

U.S. PATENT DOCUMENTS

| 595,432 | 12/1897 | Bell | 422/125 |
|---|---|---|---|
| 2,501,496 | 3/1950 | Cartwright | 422/4 |
| 2,614,820 | 10/1952 | Boydjieff | 422/116 X |
| 2,931,880 | 4/1960 | Yaffe | 422/4 X |
| 2,942,090 | 6/1960 | Diehl | 219/19 |
| 3,685,734 | 8/1972 | Paciorek et al. | 239/56 |
| 3,823,873 | 7/1974 | Miller, Jr. et al. | 239/56 X |
| 3,872,280 | 3/1975 | Van Dalen | 422/125 X |
| 3,908,905 | 9/1975 | Von Philipp et al. | 239/57 X |
| 3,959,642 | 5/1976 | Torro | 422/125 X |
| 3,990,848 | 11/1976 | Corris | 422/116 X |
| 3,993,444 | 11/1976 | Brown | 422/116 |
| 4,078,891 | 3/1978 | Madjar | 422/124 X |
| 4,102,656 | 7/1978 | Koritz | 422/124 X |
| 4,166,087 | 9/1979 | Cline et al. | 422/116 X |
| 4,214,146 | 7/1980 | Shimanski | 422/306 X |
| 4,229,415 | 10/1980 | Bryson | 422/116 X |
| 4,346,059 | 8/1982 | Spector | 422/125 |
| 4,367,203 | 1/1983 | Landsberger | 422/306 X |
| 4,374,571 | 2/1983 | Hirvela | 239/56 X |

Primary Examiner—Barry S. Richman
Assistant Examiner—William R. Johnson
Attorney, Agent, or Firm—Michael Ebert

[57] ABSTRACT

An aroma-generating unit adapted to periodically discharge into the atmosphere bursts of aromatic vapor, the non-aromatic intervals between the bursts having a duration sufficient to avoid desensitizing the olfactory response of those exposed to the unit. The unit includes a hollow case whose upper wall has a vent therein and whose side wall has a slot to receive a replaceable cartridge provided with a porous mat impregnated with an aromatic liquid. When fully inserted, the cartridge is disposed below the vent and serves to define an air-confined chamber within the case. Disposed in this chamber is an electrical heater that is periodically energized by power pulses to heat and expand the confined air and to produce a positive pressure in the chamber forcing the heated air through the impregnated mat to rapidly volatilize the liquid and to produce bursts of aroma which are discharged into the atmosphere through the vent, which bursts are separated by relatively long, non-aromatic intervals.

3 Claims, 6 Drawing Figures

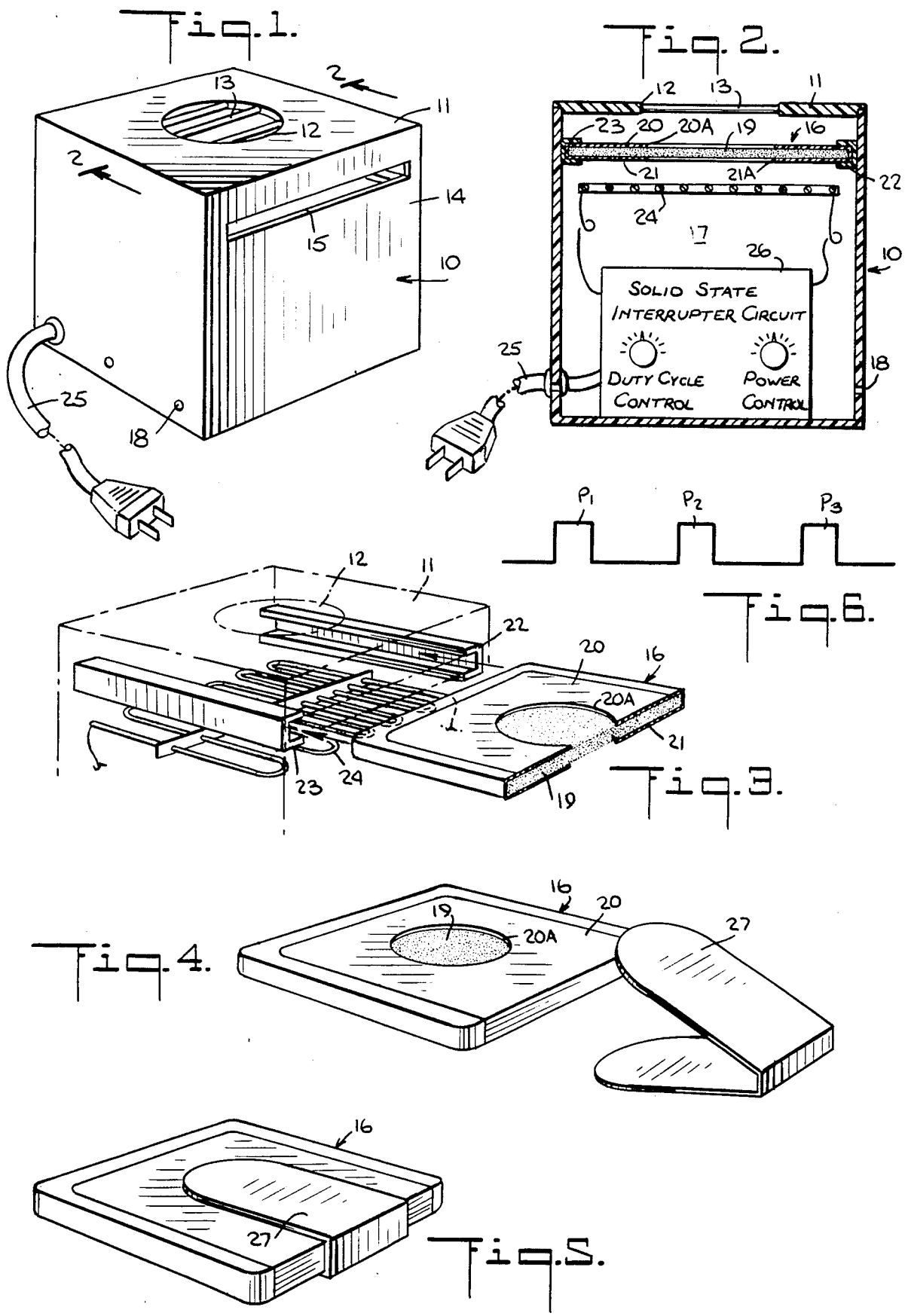

AROMA-GENERATING UNIT

BACKGROUND OF THE INVENTION

This invention relates generally to aroma-generators, and more particularly to a unit adapted to periodically discharge into the atmosphere bursts of aroma, the non-aromatic intervals between the bursts having a duration sufficient to avoid desensitizing the olfactory response of those exposed to the unit.

As used herein, the term "aroma" is not limited to pleasant or savory smells, but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and other yielding altogether new scents. Perfumes today are largely blends of natural and synthetic scents and of fixatives which equalize vaporization and enhance pungency. In most liquid scents the ingredients are combined with alcohol.

Various types of spray devices or dispensers are known for emitting aromas. Thus the patent to Dearling, U.S. Pat. No. 4,084,732, disclosed a dispenser for wafting into the atmosphere an insecticide, a pleasant smelling scent or any other aroma, this being accomplished by means of a pressurized container. When the actuating button of this container is pressed, a dispersant is released onto an absorbant material, the absorbent dispersant permeating the atmosphere.

Similarly, the Sekiguchi et al. U.S. Pat. No. 3,679,133 discloses a perfume dispenser which includes a sponge-like head that receives and exudes a charge of perfume. In the spray aerosol can disclosed in the Harrison U.S. Pat. No. 3,972,473, an absorptive ring is impregnated with an air-freshening fragrance and released into the atmosphere. U.S. Pat. Nos. 1,921,821; 3,410,488; and 3,441,353 are along similar lines, for they show wicks and other absorptive materials to accept and emit a perfume or other odoriferous liquid.

In my prior U.S. Pat. No. 4,200,229, entitled, "Aroma-Dispensing Cartridge and Holder Assembly," the assembly is designed for installation in an automobile interior for charging this interior with a pleasant or stimulating fragrance. The cartridge includes a bottle filled with a liquid scent, a suction pump being supported on the stopper of the bottle. When actuated, the pump sprays the scent onto a pad of absorbent material.

The difficulty with an aroma dispenser which functions to spray a charge of liquid onto a pad of absorbent material is that at ambient temperature the liquid, even when it has a high alcohol content, is slow to volatilize; hence the resultant odor, though of sufficient strength in the confines of an automotive interior, may lack adequate intensity in those environments which are relatively open, such as the living room or bedroom of a home.

It is known to promote vaporization of aroma-producing liquids by means of an electric bulb which also generates heat. Thus the Eisner U.S. Pat. No. 2,372,371 shows a pad saturated with a deodorant held in a small container mounted directly on the bulb. Similar bulb arrangements to promote vaporization are disclosed in the Gudeman U.S. Pat. No. 1,403,548; the Fusay et al. U.S. Pat. No. 2,557,501; and the Schlesinger U.S. Pat. No. 2,435,756. Also of background interest are the prior patents cited in my above-identified copending application now U.S. Pat. No. 4,346,059.

In my copending patent application, there is disclosed an aroma generator in which a pad of porous material impregnated with an aroma-producing liquid is disposed under a vent inm a substantailly enclosed housing. An electrical heating element placed in the housing acts to heat and expand the air confined therein to create a positive air pressure producing a pressure differential between the heated air and the atmosphere above the vent, as a consequence of which the heated air is driven through the pad to rapidly volatilize the liquid and exude an aromatic vapor through the vent into the atmosphere.

The olfactory organs are chemi-receptors which are stimulated by minute quantities of gases or vapors in air as low as one part in one million of air. The olfactory cells are connected with the brain by the fibers of the olfactory nerves. The perception of smell by an individual's brain is such, that if a given smell persists, the individual ceases to be aware of the smell, for he makes an accomodation to the odor which is then treated as the prevailing environment. Thus one who first enters a hospital environment becomes immediately conscious of an antiseptic odor, but his sensitivity thereto diminishes and virtually disappears if the individual remains in this environment. When, however, he leaves the hospital and is exposed to the outside atmosphere, he quickly senses this change.

Thus the operation of the olfactory system is such that it is highly responsive to a change in the nature or level of an aroma but is desensitized when the prevailing odor attains a steady state condition. Hence in a room having an aroma generator of the type disclosed in my copending application in which an aromatic vapor is continuously exuded, persons in the room subjected to the vapor cease in time to become aware of the aroma, and the generator, even though it continues to operate, serves no useful purpose.

SUMMARY OF THE INVENTION

In view of the foregoing, the main object of this invention is to provide an aroma-generating unit which functions to freshen or scent the air in the room in which the unit is placed, the unit acting to periodically discharge into the room atmosphere bursts of aromatic vapor, the non-aromatic intervals therebetween having a duration sufficient to avoid desensitizing the olfactory response of those exposed to the vapor.

More particularly, an object of this invention is to provide a unit which makes use of replaceable cartridges having a mat impregnated with an aroma-producing liquid, so that when a given cartridge is exhausted, it may be replaced with a cartridge generating the same or a different aroma.

Also an object of this invention is to provide a unit of the above type which operates efficiently and reliably, and which may be manufactured at low cost.

Briefly stated, these objects are attained in a unit which includes a hollow case whose upper wall has a vent therein and whose side wall has a slot to receive a replaceable cartridge provided with a porous mat impregnated with an aromaa-producing liquid. When fully inserted, the cartridge is disposed below the vent and serves to define an air-confined chamber within the case.

Disposed in the chamber is an electrical heater which is periodically energized by power pulses separated by inactive intervals. The pulse-actuated heater acts to heat and expand the confined air to produce a positive pressure in the chamber, forcing the heated air through the mat to volatilize the liquid and to produce bursts of aromatic vapor which are discharged into the atmosphere through the vent. The non-aromatic intervals have a duration sufficient to permit recovery of the olfactory response of those exposed to the vapor to avoid desensitizing the response.

OUTLINE OF DRAWINGS

For a better understanding of the invention as well as other objects and further features thereof, reference is made to the following detailed description to be read in conjunction with the accompanying drawings, wherein:

FIG. 1 is a perspective view of an aroma-generating unit in accordance with the invention;

FIG. 2 is a section taken through the unit;

FIG. 3 illustrates the guides for the replaceable cartridge;

FIG. 4 illustrates, in perspective, a single cartridge and its associated seal;

FIG. 5 shows the cartridge in the sealed state; and

FIG. 6 is the waveform of the power applied to the heater.

DESCRIPTION OF INVENTION

Referring now to FIGS. 1 and 2, there is shown an aroma-generating unit in accordance with the invention, the unit including a cube-shaped cases 10 which may be formed of opaque synthetic plastic or other suitable material. In practice, case 10 may be in other geometric forms and may, for example, be cylindrical.

The upper wall 11 of the case is provided with a central vent 12 which is circular, the vent being protected by an array of bars 13. A side wall 14 has a slot 15 therein adapted to receive a flat cartridge 16 so that when fully inserted, it occupies a position directly under top wall 11 and parallel thereto. At this position, the cartridge defines within the case a confined-air internal chamber 17. The sidewalls of chamber 17 are provided with small air inlet holes 18 adjacent the base of the case.

Cartridge 16 is constituted by a mat 19 of porous material having wicking properties. This material may be fabricated of a non-woven fabric, a flexible foam plastic, blotting paper or other suitable material. Mat 19 is sandwiched between upper and lower sheets 20 and 21 provided with corresponding central openings 20A and 21A, so that when the cartridge is fully inserted, these holes lie in registration with vent 12. The edges of the cartridge may be provided with stiffening ribs.

To hold the cartridge in place, the side walls of the case are provided with a pair of channel-shaped edge rails 22 and 23. In practice, the cartridges may effectively be "floppy discs," use being made of flexible plastic film for sheets 20 and 21. In that event, a rigid platform is provided in the case rather than edge rails, the platform having a central hole which is in line with the holes in the sheets.

Supported under the cartridge in the case is a flat electrical heater 24 which in practice may be a quartz or other insulating plate having a resistance coil embedded therein. Heater 24 is connected to a power line cable 25 through a solid state interrupter circuit 26 which acts to apply periodic pulses of electrical power to the heater. In practice, this circuit may be composed of transistorized power switches which are periodically rendered conductive at a rate determined by a resistance capacitance timing circuit. The same effect may be obtained electromechanical by a motor driven interrupter switch.

In prior art aroma-generating arrangements, no pressure is applied to cause the heated air to flow primarily through an impregnated pad to promote volatilization. In the present invention, heat-producing element 24 is placed within the air-confined chamber 17 and the heat generated therein causes the air to expand to create a pressure differential between the heated air in the chamber and the external atmosphere. As a consequence, the pressurized hot air is forced through the saturated mat 19 below vent 12, thereby promoting rapid volatilization of the liquid fragrance.

While only that portion of the mat which lies between the holes in sheets 20 and 21 has air forced therethrough, liquid volatilized by this forced air flow is replaced through the wicking action by liquid from the other regions of the mat. This pressurized action serves to prevent clogging of the pores of the mat by the liquid fragrance, the tendency toward clogging being greatest with relatively heavy oil-based perfumes.

As shown in FIGS. 4 and 5, cartridge 16 is provided with a seal 27 in the form of a detachable metal or plastic clip whose flat tines cover the holes in sheets 20 and 21 so that the cartridge, when stored, is sealed to prevent the loss of liquid. In practice, the user of the unit may be provided with a stack of such sealed cartridges. Each stack may have mats impregnated with a different aroma-producing liquid. The user, therefore, may select a fragrance appropriate to the room or to a given occasion.

As pointed out previously, in order to prevent desensitization, it is essential that the aromatic vapor emitted by the unit be interrupted for an interval sufficient to permit the olfactory system to recovery its sensitivity to the aroma. This is accomplished, as shown by the power waveform in FIG. 6, by producing periodic bursts of aromatic vapor during the power pulses $P_1$, $P_2$, etc., the intervals between pulses being non-aromatic since there is no heating. In practice, the pulses may have a duration of one minute to produce aromatic vapor bursts, and the intervals therebetween a duration of 2 to 4 minutes, such that there is sufficient time for the effect of an aromatic vapor burst on the environment to diminish to the point permitting recovery of sensitivity to the next burst.

The invention is not limited to this duty cycle, for in practice, the appropriate duty cycle depends on the nature and strength of the aromatic vapor and environmental conditions. By providing a potentiometer for the heater element and a duty-cycle control for the interrupter, one may adjust the bursts of aromatic vapor to satisfy existing requirements. The control dials for this purpose may be on the case exterior.

While there has been shown and described a preferred embodiment of an aroma-generating unit in accordance with the invention, it will be appreciated that many changes and modifications may be made therein without, however, departing from the essential spirit thereof.

I claim:

1. An aroma generating unit comprising:

A. a hollow case whose upper wall has a vent therein and whose side wall has a cartridge-receiving slot;

B. a replaceable cartridge insertable in said slot to occupy a position in said case under said vent; said cartridge, when fully inserted, defining an air-confined chamber within the case, said cartridge having a porous mat having wicking properties impregnated with an aroma-producing liquid enclosed in a housing defined by a pair of sheets between which the mat is sandwiched, said sheets having corresponding central holes therein to form a port which exposes the central portion of the mat, the remaining unexposed portion of the mat acting as a reservoir for the liquid which as liquid is depleted from the central exposed portion, it is replenished by liquid wicked from the unexposed portion; and C. an electrical heater disposed in said chamber which, when energized, acts to heat and expand the confined air therein to create a positive pressure forcing the heated air through the port and the exposed portion of the impregnated mat to rapidly volatilize the liquid and to produce an aromatic vapor which is discharged into the atmosphere through said vent.

2. A unit as set forth in claim 1, wherein said heater is operated by means to cause it to be periodically energized by power pulses to produce bursts of aromatic vapor interrupted by non-aromatic intervals of sufficient duration to permit recovery of the olfactory response of those exposed to the aromatic vapor, said means being constituted by a solid state interrupter which couples said heater to a power line to produce power pulses whose duty cycle is adjustable.

3. A unit as set forth in claim 2, wherein said pulses have a duration of about one minute and the intervals a duration of at least two minutes.

* * * * *